United States Patent [19]

Carr

[11] 4,037,973

[45] July 26, 1977

[54] LIGHT SENSITIVE DEVICE FOR MEASURING PARTICLES IN A LIQUID

[75] Inventor: Larry R. Carr, West Chicago, Ill.

[73] Assignee: Optronix Inc., West Chicago, Ill.

[21] Appl. No.: 635,279

[22] Filed: Nov. 26, 1975

[51] Int. Cl.² ............................................. G01N 21/26
[52] U.S. Cl. .................................... 356/206; 250/575; 356/208
[58] Field of Search ....................... 356/206, 207, 208; 250/575

[56] References Cited

U.S. PATENT DOCUMENTS

| 3,652,850 | 3/1972 | Briggs | 356/206 |
| 3,851,976 | 12/1974 | Meier | 356/207 |
| 3,954,342 | 5/1976 | Boeke | 356/206 |

*Primary Examiner*—Vincent P. McGraw

*Attorney, Agent, or Firm*—Hill, Gross, Simpson, Van Santen, Steadman, Chiara & Simpson

[57] ABSTRACT

A device for measuring particles in a liquid, utilizing a light source for the illumination of two detectors, one through a relatively short distance and the other through a relatively long distance, with liquid to be measured passing between the light source and the two detectors. A reference signal produced by the first cell is supplied to an amplifier and indicator, and a measurement signal produced by the second detector is supplied to the amplifier and indicator, with such amplifier and indicator producing a visual indication of the concentration of particles suspended in the liquid. The two detectors and light source are contained in a small housing, remote from the amplifier and indicator, and connected to it by a flexible cable.

15 Claims, 5 Drawing Figures

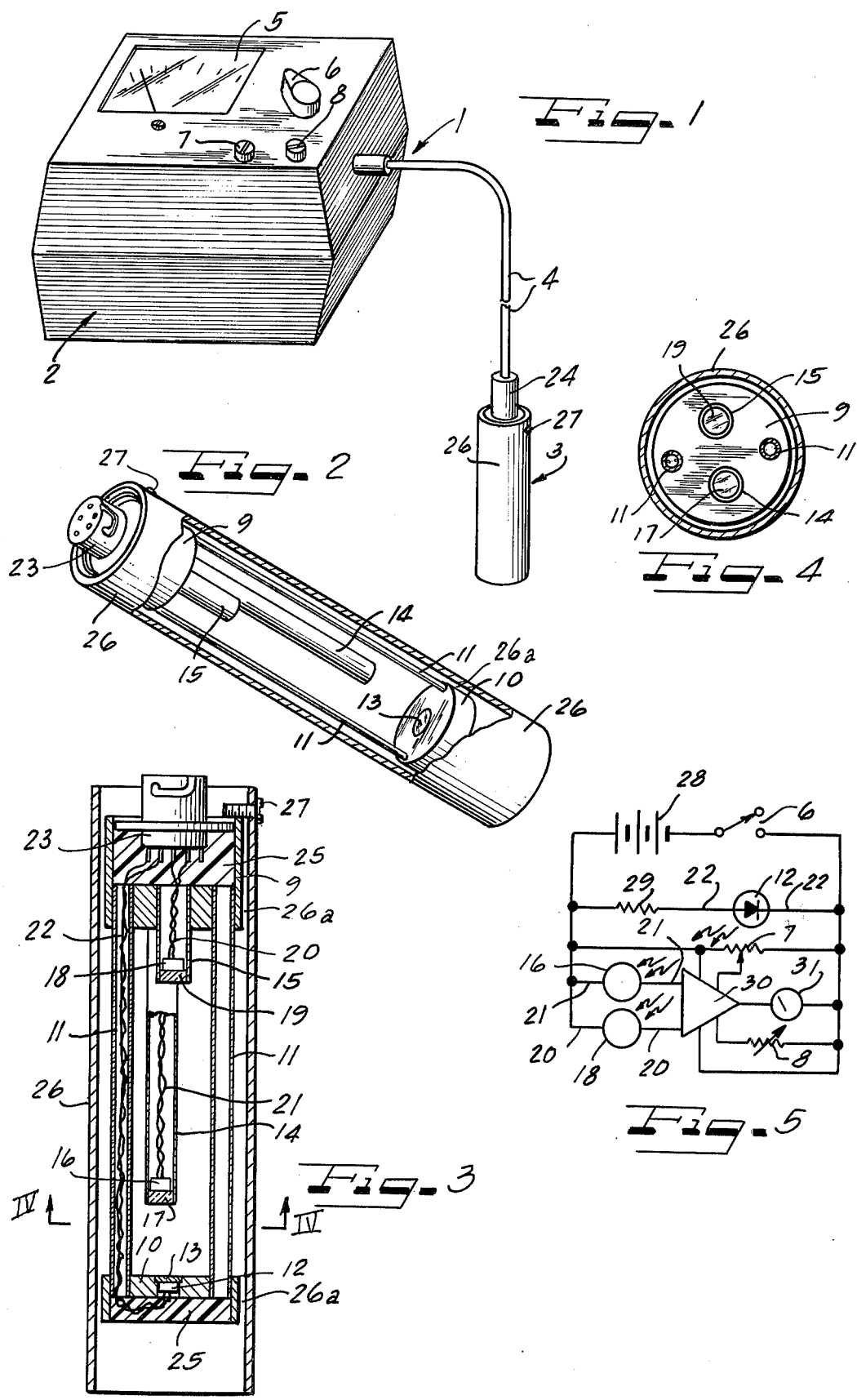

LIGHT SENSITIVE DEVICE FOR MEASURING PARTICLES IN A LIQUID

BACKGROUND OF THE INVENTION

The invention relates generally to the measurement of particles suspended in a liquid, and particularly to a device for the measurement, over a wide range of concentration, of particles suspended in large bodies of liquids such as in the tanks of waste treatment plants. In such large bodies of liquids, the solids concentrations may vary from a few mg./l. to 25,000 mg./1., and it is often advantageous to measure the concentration of suspended solids at various locations within a given tank, as well as in many tanks within a particular treatment plant. This is usually accomplished by manually drawing samples, with subsequent manual analyzation by a chemist. This is a costly and time consuming procedure and the test results are rarely available in a sufficiently short period of time to be of value for controlling the process.

Such time lag and manpower requirements can be reduced by the use of an automatic suspended solids analyzer at each point of interest. Until now, however, this has been prohibitively expensive because the large number of points and wide range of concentrations has dictated a great number of instruments.

In addition to the initial expense, the presence of a large number of instruments of this nature requires a great amount of maintenance and frequent calibration. Calibration is particularly difficult in a waste treatment plant since the instruments must be removed from their permanent mountings and remounted in a large tank containing a liquid of known concentration, and, to obtain a reliable calibration, this procedure must be performed at several concentrations. An alternate approach is to leave the instrument in its mounting and wait for the concentration of the tanks to gradually change, taking samples at various times. This procedure may take several days since the tanks in a waste treatment plant have long detention times and their contents usually do not change rapidly. When a large number of instruments are present in a given plant, and in need of frequent recalibration, the labor involved in recalibration often approaches the labor of performing the analysis by hand, and the value of the instruments is greatly diminished.

It will be appreciated that the utilization of a portable, wide-range instrument would greatly simplify this measurement problem, quickly providing answers and capable of being readily calibrated. Until now, however, this has not been possible since operation of existing arrangements by means of batteries (1) only renders the problems associated with recalibration portable, (2) the existing designs cannot measure wide ranges of concentrations, and (3) portable operation introduces new problems of its own.

The necessity for frequent recalibration is dependent upon the design of the instrument, the range of its measurements, and how it is employed. In general the causes are:

1. Changes in calibration due to changes in particle size, shape, or color.
2. Changes in instrument indications due to drift. This in turn may be due to:
    A. The temperature coefficient of the detectors means.
    B. Detector light history effects.
    C. Ambient light interference.
    D. Temperature coefficient of the emitter means.
    E. Changes in emitter intensity with source (battery) voltage.
    F. Obstruction or modification of light paths by slime or debris.
    G. Amplifier or indicator drift (electronics).

The interaction between these effects is best explained by examining them in accordance with the concentration to be measured.

In low concentrations, the most common measurement method employs the light scattering effect of suspended particles to obtain an indication. Although the exact configuration varies, in general the operation is as follows: A light source illuminates the liquid inside a light tight container and a photocell is positioned so as to receive only light scattered by the particles at some specific angle. The photocell produces only a slight background output in clear liquids and its output increases as more particles are introduced. This method has the following characteristics:

1. Extremely high sensitivity to low concentrations of particles, allowing simple circuitry.
2. Extremely high sensitivity to ambient light, necessitating a fully enclosed chamber to prevent interference.

FIG. 3. Extremely high sensitivity to particle reflectively, thus changing its response with variations in particle size, shape and color.

4. Subject to interference from the absorption and reflection of light by particles adhering to the measurement surfaces.

5. Nonlinear indications, reversing its readings in very high concentrations and thus producing ambiguous indications.

Some of the problems of light scattering instruments can be overcome by employing multiple photocells, or a compensating photocell to measure the amount of light transmitted directly through the liquid. This design modification does not eliminate the requirement for a light tight enclosure. Depending on the configuration of the photocells and electronic signal processing, the use of dual detectors can eliminate the drift associated with temperature changes. It can also reduce the effects of particles adhering to the measurement windows, if and only if, both detectors are positioned at equal angles to the incident light beam and there are no shields or other physical structures in the light beam. It should be noted that this requirement is difficult to obtain without resorting to a design that is subject to ambient light interface and this problem is aggrevated by the fact that two or more cells must be protected. Even so, light scattering techniques are still subject to the basic problem of varying indications as particle reflectivity changes.

In concentrations higher than several hundred milligrams per liter, scattering-type instruments are completely inappropriate due to their nonlinearity, and light transmission instruments are employed. These devices operate by transmission of a beam of light directly through a liquid and detection of the amount of light transmitted (or absorbed) by the particles in the liquid. In clear liquids, the transmission is 100%, decreasing as the solids content increases. Light transmission instruments have the following characteristics:

1. Reverse reading; i.e., full scale at zero concentration. 2. Logarithmetic response in many liquids.

3. Insensitivity to reasonably large variations in particle size, shape, and color (reflectivity).

4. Subject to offsets as slime or debris accumulates on the measurement surfaces. These offsets affect all readings equally; for example, a given amount of debris may produce a 50ppm error and this 50 ppm error will be constant at any reading.

5. Subject to ambient light interference, but to a lesser degree than scattering instruments.

6. Upper limit of measurement determined by detector sensitivity and light source strength.

Both light transmission and light scattering instruments are subject to errors due to changes in either the light source, the detector, or debris on the windows through which the light beams passes.

While nearly all of the characteristics of a transmission or scattering-type instrument can be tailored to the measurement parameters of a particular liquid or environment, previous workers in the field have been unable to produce an efficient portable, wide range instrument.

Available suspended solids analyzers, having any degree of precision, have as a fundamental requirement of their design one of the following objections:

1. A highly focused optical system with multiple lense or baffles which are fragile and cannot withstand abuse. (When shock mounted, such structures are generally heavy and bulky.)

2. Special sample handling, such as pouring into a test tube or pumping through a pipe.

3. Intricate structures that allow rapid accumulation of debris.

4. Complicated mechanisms or methods of calibration.

5. Highly inefficient use of light, resulting in high power consumption and bulky power supplies.

BRIEF SUMMARY OF THE INVENTION

The invention has among its objects the production of a suspended solids analyzer which is capable of wide range applicability in widely varying liquids, and yet is readily portable, being small enough to be easily handled and maneuvered, while at the same time being of rugged construction capable of withstanding relentless abuse.

The invention further has among its objects, the production of such an analyzer which can automatically compensate for the presence of slime and debris on the measurement surfaces, is easily cleaned and maintained, and simple to calibrate.

These results are achieved in the present invention by the utilization of a sensing unit having a pair of light sensors, i.e., photo detectors, which are disposed in the path of light emitted by a light source such as a light emitting diode, also carried by the unit. The outputs of the respective photo detectors are conducted to a main unit and supplied to a dividing amplifier contained therein, the output of which is directly proportional to the ratio of the output values of the respective photo detectors. The amplifier thus is sensitive to the ratio of the two output values and may be employed as a direct measurement of concentration. A meter thus may be connected to the output of the dividing amplifier, calibrated in units of concentration, and means may be provided for achieving a zero adjustment as well as adjustment of the amplifier.

BRIEF DESCRIPTION OF THE DRAWINGS

In the drawings, wherein like reference characters indicate like or corresponding parts:

FIG. 1 illustrates a portable analyzer in accordance with the invention;

FIG. 2 is an oblique view of the sensing unit of the analyzer;

FIG. 3 is a longitudinal section through the sensing unit of FIG. 2, with portions broken away to show the details thereof;

FIG. 4 is a sectional view, taken approximately on the line IV—IV of FIG. 3; and FIG. 5 is a schematic diagram of the electrical circuit of the analyzer.

DETAILED DESCRIPTION OF A PREFERRED EMBODIMENT

Referring to the drawings, and particularly to FIG. 1, the reference numeral 1 indicates generally an analyzer in accordance with the invention, illustrated as comprising a main analyzer unit, indicated generally by the reference numeral 2, and a cooperable sensing unit, indicated generally by the reference numeral 3, which is operatively connected to the unit 2 by a flexible cable 4, of suitable length.

The sensing unit 3 is adapted to be immersed in the liquid involved, and contains the necessary sensing elements, responsive to the suspended solids of the liquid to be tested, while the unit 2 contains the circuitry for actuating a suitable indicator, such as a meter 5, and may be provided with suitable controls, such as an on-off switch 6, which if desired also, could be constructed to function as a range switch, and suitable adjusting controls 7 and 8, for example, for use in calibration and output adjustments.

Referring to FIGS. 2-4, the sensing unit 3 comprises a pair of spaced base members 9 and 10 which are operatively connected in rigid relation by a pair of rods 11, at least one of which is hollow. The lower member 10 is provided with a light source 12, protected by a window 13 facing the general direction of the upper member 9. Carried by the latter and depending downwardly therefrom toward the light source 12, for example a light-emitting diode, are a pair of detector holders 14 and 15, the holder 14 being provided with a light detector, i.e., a photo detector 16, with the adjacent free end of the member 14 being closed by a window 17. In like manner, the hollow member 15 is provided with a photo detector 18 with the adjacent free end of the holder 15 being closed by a light transmissive window 19. The holders 14 and 15 are connected to their respective base members 9 and 10 in watertight relation and in like manner the windows 17 and 19, as well as the window 13 are connected to their associated members in watertight relation.

The connecting electrical conductors 20 and 21 for the respective detectors 16 and 18 extend upwardly through their respective holders 14 and 15, while the light source 12 is adapted to be supplied with current by conductors 22, extending from the source 12 upwardly through the adjacent hollow supporting rod 11 to the base member 9, where all of the respective conductors are operatively connected to a suitable female connector socket 23 adapted to be operatively connected to the cable 4 by a cooperable male connector 24.

As clearly illustrated in FIG. 3, the outermost ends of the respective base members 9 and 10 may be closed in watertight relation by means of a suitable sealant 25, whereby the respective photo detectors 16, 18 and light source 12 are completely protected from the liquid involved, which sealant also may maintain the respective parts in fixed relation.

A cover 26 having slightly larger dimensions than the base members 9, 10 of the sensing unit 3, for example having an inner diameter of 1/32 to 3/32 inch greater than the outer diameter of the base members 9 and 10, may be slipped over the latter to prevent ambient light from entering the unit. Suitable means, for example a rivet or screw 27 or prevents the cover 13 from dropping off. The gap 26a, between the base members 9, 10 and the cover 26, provides for ingress and egress of liquid for measurement.

FIG. 5 schematically illustrates a typical electrical circuit which can be employed with the aforementioned light source 12 and photo detectors 16, 18. Power is supplied by a suitable battery 28 controlled by a suitable switch 6. Upon closing the switch 6 the light source 12 is energized via conductors 22, and current limiting resistor 29. A dividing amplifier 30 is also energized. Its input consists of the two currents flowing from photo detectors 16 and 18 via wires 20, 21, respectively, and is directly proportional to the second photo detector 18 current divided by the first photo detector 16 current. The dividing amplifier 30 is not sensitive to the absolute values of these photo currents, only their ratio.

Potentiometer 7 provides a means of zero adjustment while variable resistor 8 is used to vary the gain of dividing amplifier 30. A voltmeter 5 is connected to the output of the dividing amplifier 30 and is calibrated in units of concentration.

In operation of the instrument power is applied by turning the switch 6, energizing the dividing amplifier 30, and the light source 12. Light emitted from the light source 12 passes through the window 13 and up to the window 17 of the first photo detector 16, and also up to the window 19 of the second photo detector 18. The second photo detector 18, as illustrated, is spaced a greater distance from the light source 12 than the first photo detector 16, and therefore it receives less light and conducts less current.

In calibration of the instrument the sensing unit 3 initially is immersed in a clear liquid (zero concentration) and then in liquid of known high concentration. When immersed in the clear liquid, the photo detector currents are unequal and the meter 31 indicates some upscale value. The potentiometer 7 is then adjusted, providing a variable offset potential to the dividing amplifier 30 which causes its output to decrease to zero, thus producing a "0" indication on the volt meter 31. The sensing unit 3 is then immersed in a liquid of known high concentration. Particles suspended in the liquid absorb light, and the amount of light that reaches each photo detector decreases. Since the second photo detector receives light from the light source through a greater depth of liquid it receives a proportionally greater decrease than the first photo detector. The two photo currents that pass into the dividing amplifer are thus changed appreciable and the dividing amplifier output increases accordingly, producing an increased deflection on the voltmeter. Variable resistor 8, (which determines the gain of the dividing amplifier 30) is adjusted so that the voltmeter 5 indicates the concentration of the liquid. This completes the calibration.

Once calibrated in the above manner the instrument is ready for measurement of a wide range of liquids without further adjustment.

It will be appreciated that since a portable sensor may be used to measure the suspended solids concentration of several liquids of widely differing temperature in rapid succession, temperature compensation is critical. Previous devices have either ignored this problem or have had to rely on elaborate isolation of the detector and light source from the liquid. The present invention solves this problem in two steps. The first is the use of two detectors of identical construction and the dividing amplifier. As the temperature changes the photo detector currents change by equal percentages and the dividing amplifier output remains constant since it is sensitive to the ratio of the two currents only and not their absolute values.

It will further be appreciated that while this form of temperature compensation is excellent in the long term, it also compensates for short term, rapid temperature transients that occur when the sensing unit is subjected to sudden heating or cooling when it is first immersed in a liquid. The unique structure of the invention places both photo detectors in identical thermal paths to the liquid so that they not only achieve thermal equilibrium with the liquid rapidly, but at equal rates. As can be seen from FIG. 3 both cells are positioned well away from any thermal mass and they are in close thermal proximity to the liquids. As a practical matter this construction allows reliable indications to be made within a minute or two after a 30°-40° F temperature change. Normally such instruments require 5 to 10 minutes, or longer, to stabilize, greatly limiting the number of measurements that can be made in a given time period. Waiting for an instrument to stabilize while holding it, for example, over a hand rail into a large tank is tiresome, and operators have a tendency to not wait long enough, and to estimate the stabilized value. This reduces the precision of the resulting measurement. The invention thus greatly increases both the number of measurements that can be made and their individual precision.

Another factor which previous devices have failed to properly solve relates to the effects of "light history" of the photo detectors. When a sensing unit is used outside, the detectors may be alternatively subjected to bright sunlight and low light (in a dark liquid). The photo cells react in a manner similar to the human eye in that they are at first "blinded" by sunlight and cannot react properly when first submerged in a dark liquid. The obvious solution to this problem is to shield out external light, but the manner of shielding for a portable sensing unit is critical and has not heretofore been effectively achieved. For a portable sensing unit the shield must be sufficiently tight to prevent blinding by sunlight, yet it must allow the liquid to freely flow within the measurement area so as to obtain a representative sample. In addition, for application in waste treatment plants, it is important that there be no structures than can clog, catch stringy debris, or otherwise impede the hydraulic or optical paths. Also, the measurement area must be simple to inspect and clean.

The invention solves this problem by the use of the cover shield 26 which is slightly larger than the upper and lower base member 9, 10. The cover, being held in place by gravity against the rivet or screw 27, can be readily slipped upward for cleaning or inspection of the unit. The small gap between the cover and the base members allows liquid to freely pass, yet greatly attenuates external light. Any light that does pass through the gap, separating the upper member 9 and the cover 26, does not interfere with the measurement since both photo detectors are facing downward, away from the light. Any light that does pass through the gap separating the lower base member 10 and the cover 26 appears at the same plane as the source window 31 and therefore has the effect of increasing the intensity of the light source.

Changes in the intensity of the light source do not effect the indications since a given increase or decrease in light intensity produces an equal percentage increase or decrease in the photo currents. In like manner, slime coating on the photo detector windows or source windows do not effect the indications.

Having thus described my invention it will be obvious that although various minor modifications might be suggested by those versed in the art, it should be understood that I wish to embody within the scope of the patent granted hereon all such modifications as reasonably, and properly come within the scope of my contribution to the art.

I claim as my invention:

1. A sensing unit for suspended solids measurements and the like, comprising a single light source, a pair of photo detectors disposed on substantially a common light path of said source at different distances with respect thereto, with the liquid to be measured adapted to be disposed therebetween, means for supporting said source and detectors in fixed relation and in sealed relation with respect to the liquid to be measured, conductor means operatively connected to said source and detectors for connecting the same in an operative measuring circuit, and tubular opaque shield means cooperable with said supporting means to define a fluid chamber containing said source and detectors, said fluid chamber being provided at opposite ends of said tubular shield means with passageways for the ingress and egress of liquid relative to said fluid chamber.

2. A sensing unit according to claim 1, wherein said supporting means comprises upper and lower base members, the light source being carried by the lower base member and the photo detectors by the upper base member, with said base members thus defining a measuring space therebetween.

3. A sensing unit according to claim 2, wherein said supporting means includes respective rods connecting said base members in rigid relation, at least one of which rods is hollow and forms a conduit for conductor means to said light source.

4. A sensing unit according to claim 2, wherein said tubular shield means comprises a tubular shield member open at its ends encircling said measuring space, with said tubular member being closed at its ends by the respective base members.

5. A sensing unit according to claim 4, wherein said cover shield is of a size to provide said liquid passages between the base members and the cover shield for said liquid ingress and egress.

6. A sensing unit according to claim 2, wherein said photo detectors are mounted in tubular holders extending downwardly from said upper base member with said photo detectors disposed adjacent the respective free lower ends of the holders, each of said lower ends being sealed by a respective permeable window.

7. A device for the measurement of particles suspended in a liquid, comprising a sensing unit having a liquid-receiving chamber in which are disposed a single light source and two photo detectors arranged on substantially a common light path of said source at different distances therefrom, with the liquid to be measured adapted to be disposed therebetween, and amplifier means to which the output currents of the respective photo detectors are supplied, for forming a value representative of the ratio between the two photo detector currents, the magnitude of which value is proportional to the particle concentration of the liquid being measured.

8. A device according to claim 7, wherein said amplifier is connected to provide a current ratio of (the photo detector with longer light path)/(the photo detector with shorter light path).

9. A device according to claim 7, comprising in further combination visual indicator means connected to the output of said amplifier, manually adjustable means for effecting a zero adjustment of said indicating means, and further manually adjustable means for varying the operation of said amplifier.

10. A device according to claim 7, wherein said sensing unit includes means for supporting said source and detectors in fixed relation and in sealed relation with respect to the liquid to be measured, conductor means operatively connected to said source and detectors for connecting the same in an operative measuring circuit, and opaque shield means cooperable with said supporting means to define a fluid chamber containing said source and detectors, said unit being provided with passageways for the ingress and egress of liquid relative to said fluid chamber.

11. A device according to claim 10, wherein said supporting means comprises upper and lower base members, the light source being carried by the lower base member and the photo detectors by the upper base member, with said base members thus defining a measuring space therebetween.

12. A device according to claim 11, wherein said supporting means includes respective rods connecting said base members in rigid relation, at least one of which rods is hollow and forms a conduit for conductor means to said light source.

13. A device according to claim 11, wherein said measuring space is enclosed by a tubular shield member encircling the same and closed at its ends by the respective base members.

14. A device according to claim 13, wherein said cover shield is of a size to provide said liquid passages between the base members and the cover shield for said liquid ingress and egress.

15. A device according to claim 11, wherein said photo detectors are mounted in tubular holders extending downwardly from said upper base member with said photo detectors disposed adjacent the respective free lower ends of the holders, each of said lower ends being sealed by a respective permeable window.

* * * * *